(12) United States Patent
Le Gette et al.

(10) Patent No.: US 6,502,247 B2
(45) Date of Patent: Jan. 7, 2003

(54) APPARATUS AND METHOD FOR MAKING AN EAR WARMER HAVING INTERIOR SEAMS

(75) Inventors: Brian Edward Le Gette, Severna Park, MD (US); Justin Saul Werner, Millersville, MD (US)

(73) Assignee: Gray Matter Holdings LLC, Baltimore, MD (US)

( * ) Notice: Subject to any disclaimer, the term of this patent is extended or adjusted under 35 U.S.C. 154(b) by 0 days.

(21) Appl. No.: 09/978,591

(22) Filed: Oct. 18, 2001

(65) Prior Publication Data

US 2002/0020003 A1 Feb. 21, 2002

Related U.S. Application Data

(63) Continuation of application No. 09/521,241, filed on Apr. 5, 2000, now Pat. No. 6,332,223.

(51) Int. Cl.[7] .................................. A42B 1/06
(52) U.S. Cl. ........................................ 2/209
(58) Field of Search ............................ 2/209; 128/857, 128/864, 866; 181/129, 137

(56) References Cited

U.S. PATENT DOCUMENTS

| | | | | |
|---|---|---|---|---|
| 138,894 A | * | 5/1873 | Isidor | 2/209 |
| 548,738 A | | 10/1895 | Ballard | |
| 1,179,473 A | | 4/1916 | Taylor | |
| 1,326,875 A | | 12/1919 | Miller | |
| 1,398,958 A | | 12/1921 | Basch | |
| 1,577,183 A | | 3/1926 | Dowiarz | |
| 1,628,483 A | | 5/1927 | Wiegand et al. | |
| 1,988,880 A | | 1/1935 | Strouse | |
| 2,070,216 A | | 2/1937 | Rosenberg | |
| 2,216,954 A | | 10/1940 | McDonough | |
| 2,246,031 A | | 6/1941 | Baritz et al. | |
| 2,314,782 A | | 3/1943 | Goretsky | |
| 2,333,392 A | * | 11/1943 | Rosenzweig | 2/195.5 |
| 2,405,326 A | * | 8/1946 | Plotsky | 2/209 |
| 2,420,245 A | | 5/1947 | Hurst | |

(List continued on next page.)

FOREIGN PATENT DOCUMENTS

| | | |
|---|---|---|
| FR | 1 353 524 | 1/1964 |
| FR | 2 532 838 | 3/1984 |
| FR | 2 536 253 | 5/1984 |
| JP | 60-29141 | 2/1985 |
| JP | 6-244188 A | 12/1985 |
| JP | 62-21016 | 2/1987 |
| JP | 63-20232 | 6/1988 |
| JP | 6-351090 A | 12/1994 |
| JP | 10-257581 | 9/1998 |
| SE | 294003 | 1/1954 |
| WO | WO0 745 364 A3 | 12/1996 |
| WO | WO01/76402 A1 | 10/2001 |

OTHER PUBLICATIONS

Advertisement: The "PODZ" ear warming eye glass retainer, Shred Alert Products of Hood River, Oregon.

Primary Examiner—Rodney M. Lindsey
(74) Attorney, Agent, or Firm—Cooley Godward LLP

(57) ABSTRACT

An ear warmer comprises a set of membranes and a frame. The set of membranes collectively defines an outer perimeter. The set of membranes is attached along the outer perimeter to define an attachment portion. The attachment portion is entirely disposed within an interior of the set of membranes. The frame is disposed within the interior of the set of membranes.

42 Claims, 7 Drawing Sheets

U.S. PATENT DOCUMENTS

| | | |
|---|---|---|
| 2,532,852 A | 12/1950 | Oaks |
| 2,586,644 A | 2/1952 | Gilbert |
| 2,615,169 A | 10/1952 | Maxant |
| 2,671,221 A | 3/1954 | Triplett |
| 2,717,930 A | 9/1955 | Hintz |
| 2,858,544 A | 11/1958 | Roth |
| 3,087,028 A | 4/1963 | Bonnin |
| 3,156,923 A | 11/1964 | Timm |
| 3,249,949 A | 5/1966 | Rosenberg et al. |
| 3,308,480 A | 3/1967 | Elder |
| 3,447,160 A | 6/1969 | Teder |
| 3,509,580 A | 5/1970 | Rubenstein et al. |
| 3,787,899 A | 1/1974 | Krawagna |
| 4,065,176 A | 12/1977 | Fontana |
| 4,277,847 A | 7/1981 | Florio |
| 4,404,434 A | 9/1983 | Pelt et al. |
| 4,445,005 A | 4/1984 | Furuhashi |
| 4,463,223 A | 7/1984 | Yamanoi et al. |
| 4,516,274 A | 5/1985 | Buckland |
| 4,546,215 A | 10/1985 | Ferraro |
| 4,615,185 A | 10/1986 | Bollinger |
| 4,654,898 A | 4/1987 | Ishikawa |
| 4,660,229 A | 4/1987 | Harris |
| 4,662,590 A | 5/1987 | Hungerford, Jr. |
| 4,669,129 A | 6/1987 | Chance |
| 4,670,911 A | 6/1987 | Dunford |
| 4,727,599 A | 2/1988 | Rappaport et al. |
| 4,747,145 A | 5/1988 | Wiegel |
| 4,776,042 A | 10/1988 | Hanson et al. |
| 4,776,044 A | 10/1988 | Makins |
| 4,783,822 A | 11/1988 | Toole et al. |
| 4,791,684 A | 12/1988 | Schwartz |
| 4,858,248 A | 8/1989 | Goldsmith et al. |
| 4,864,619 A | 9/1989 | Spates |
| 4,872,219 A | 10/1989 | Duncan |
| 4,907,266 A | 3/1990 | Chen |
| 4,918,757 A | 4/1990 | Janssen et al. |
| 4,982,451 A | 1/1991 | Graham |
| 5,033,094 A | 7/1991 | Hung |
| 5,038,412 A | 8/1991 | Cionni |
| 5,117,464 A | 5/1992 | Jones et al. |
| 5,164,987 A | 11/1992 | Raven |
| 5,201,856 A | 4/1993 | Edwards |
| 5,257,420 A | 11/1993 | Byrne, Jr. |
| 5,327,178 A | 7/1994 | McManigal |
| 5,339,467 A | 8/1994 | Brinkley |
| 5,545,859 A | 8/1996 | Ullrich |
| 5,551,089 A | 9/1996 | Whidden |
| 5,749,099 A | 5/1998 | Voorhees |
| 5,821,468 A | 10/1998 | Urella et al. |
| 5,835,609 A * | 11/1998 | LeGette et al. ............... 2/209 |
| 6,016,574 A | 1/2000 | Chen |
| 6,065,157 A | 5/2000 | Felman |
| 6,104,824 A | 8/2000 | Ito |
| 6,332,223 B1 | 12/2001 | Le Gette et al. |

* cited by examiner

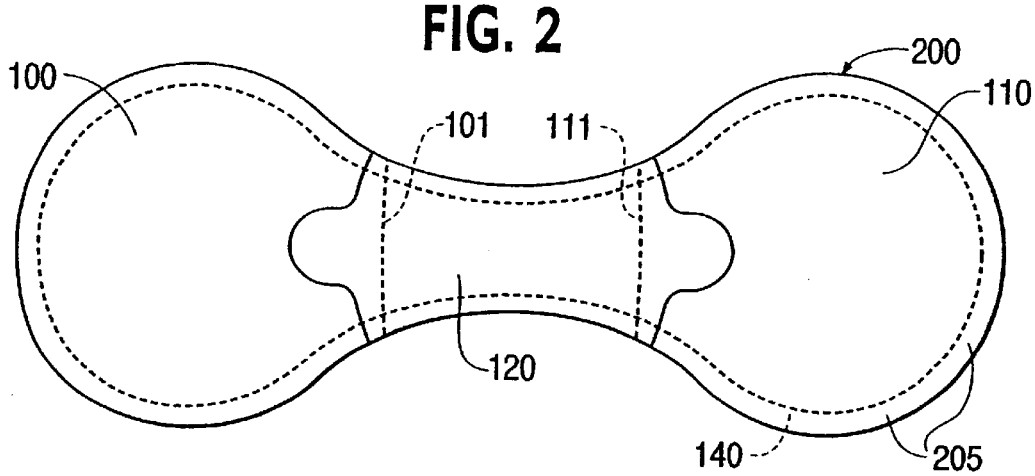
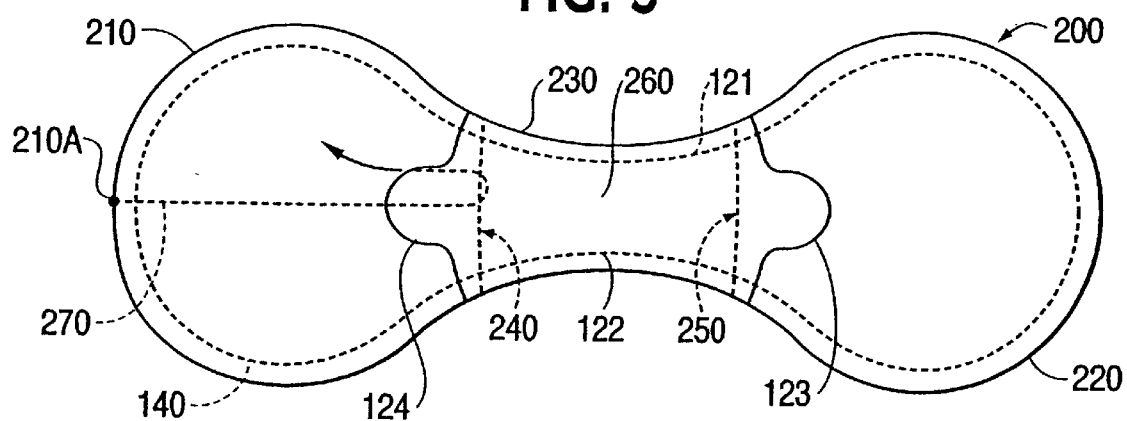
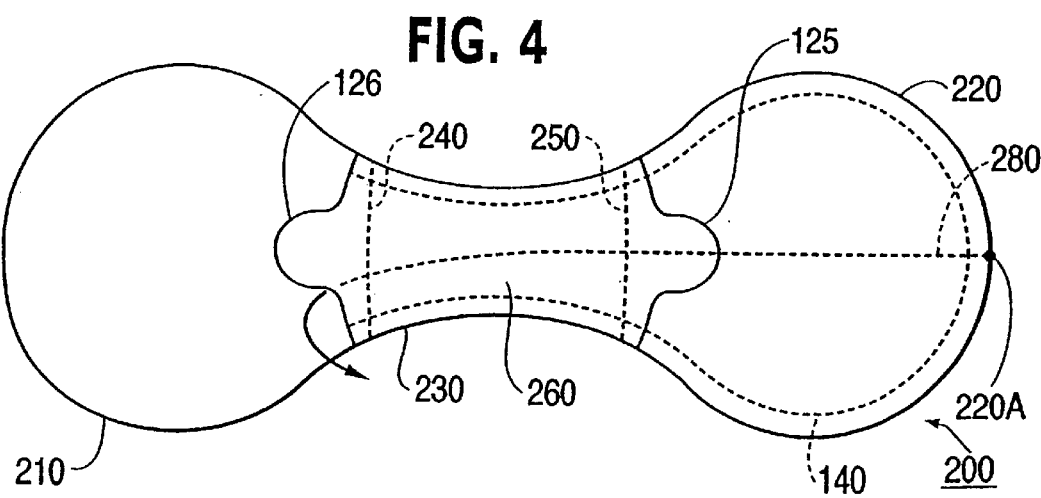

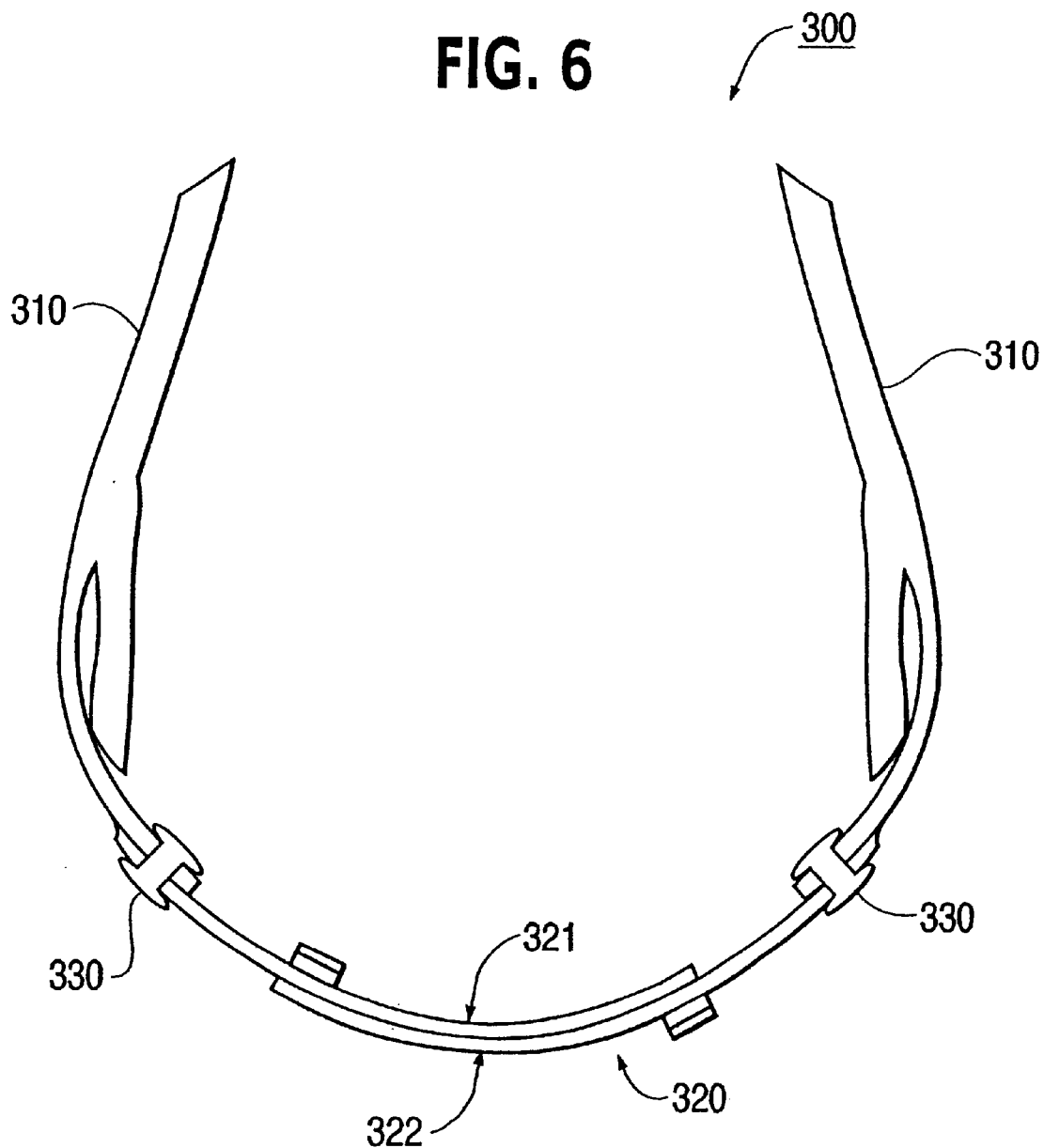

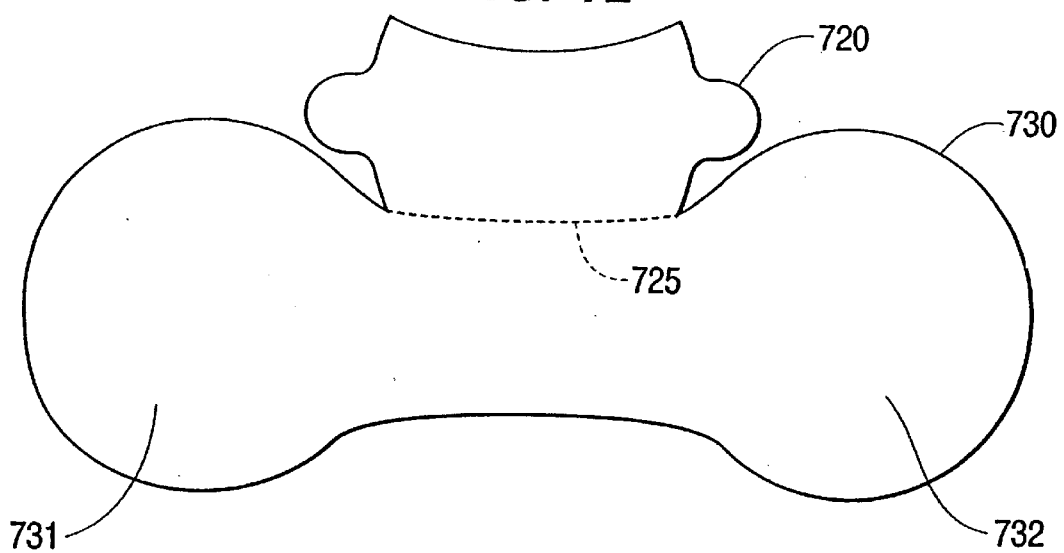
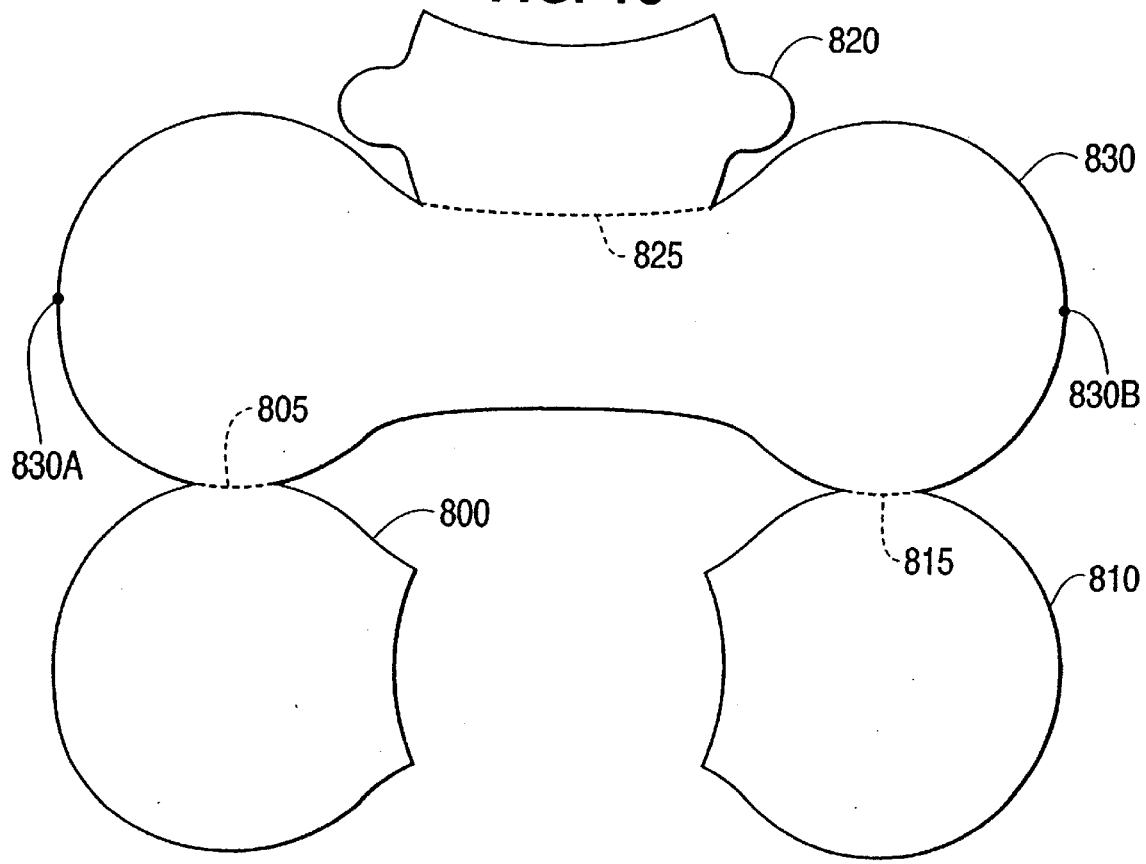

US 6,502,247 B2

APPARATUS AND METHOD FOR MAKING AN EAR WARMER HAVING INTERIOR SEAMS

CROSS-REFERENCE TO RELATED APPLICATION

This application is a continuation of U.S. patent application Ser. No. 09/521,241, entitled "Apparatus and Method for Making an Ear Warmer Having Interior Seams," filed Apr. 5, 2000, now U.S. Pat. No. 6,332,223 B1, the entire disclosure of which is incorporated herein by reference.

BACKGROUND

The present invention relates to an ear warmer device. More specifically, the present invention relates to an apparatus and a method for making an ear warmer having interior seams.

U.S. Pat. No. 5,835,609 entitled "Ear protection Device" relates to an ear warmer device having a shell that is constructed from multiple layers of fabric, and is incorporated herein by reference. The multiple layers of fabric are sewn along the collective perimeter of the fabric layers. The sewn seam is on the exterior of the ear warmer and can be covered by a binding sewn on top of the seam. A frame can be then inserted into the interior of the ear warmer shell formed by the sewn fabric layers to complete the assembly of the ear warmer.

Although the binding over the exterior-facing sewn seams provides an aesthetically pleasing appearance, the binding is an added expense and requires another step in the manufacturing process. Thus, it is desirable to provide a way to assemble the ear warmer without having exterior-facing sewn seams while also not requiring an additional component such as binding.

SUMMARY OF THE INVENTION

An ear warmer comprises a set of membranes and a frame. The set of membranes collectively defines an outer perimeter. The set of membranes is attached along the outer perimeter to define an attachment portion. The attachment portion is entirely disposed within an interior of the set of membranes. The frame is disposed within the interior of the set of membranes.

BRIEF DESCRIPTION OF THE DRAWINGS

FIG. 2 illustrates an arrangement of an ear warmer shell during an interim step in an assembly process, according to an embodiment of the present invention.

FIGS. 3, 4 and 5 illustrate top views of the ear warmer shell of FIG. 2 at different steps in a method for assembling an ear warmer, according to an embodiment of the present invention.

FIG. 6 illustrates a top view of a frame that can be disposed within an ear warmer shell to form an ear warmer, according to an embodiment of the present invention.

FIG. 12 illustrates a set of membranes for use in constructing an ear warmer, according to another embodiment of the present invention.

FIG. 13 illustrates a membrane for use in constructing an ear warmer, according to yet another embodiment of the present invention.

DETAILED DESCRIPTION

An ear warmer comprises a set of membranes and a frame. The set of membranes collectively defines an outer perimeter. The set of membranes is attached along the outer perimeter to define an attachment portion. The attachment portion is entirely disposed within an interior of the set of membranes. The frame is disposed within the interior of the set of membranes.

The term "attachment portion" is defined herein as a portion of the set of membranes between the attachment and the outer edge of the membranes. For example, the ear warmer membranes can be sewn together along their collective perimeter and then turned inside out. In such a case, the sewn seam as well as the extra portion of the membranes between the sewn seam and the outer edge of the membranes are inside the ear warmer; the frame can be inserted into the interior of the membranes.

Figure 1:
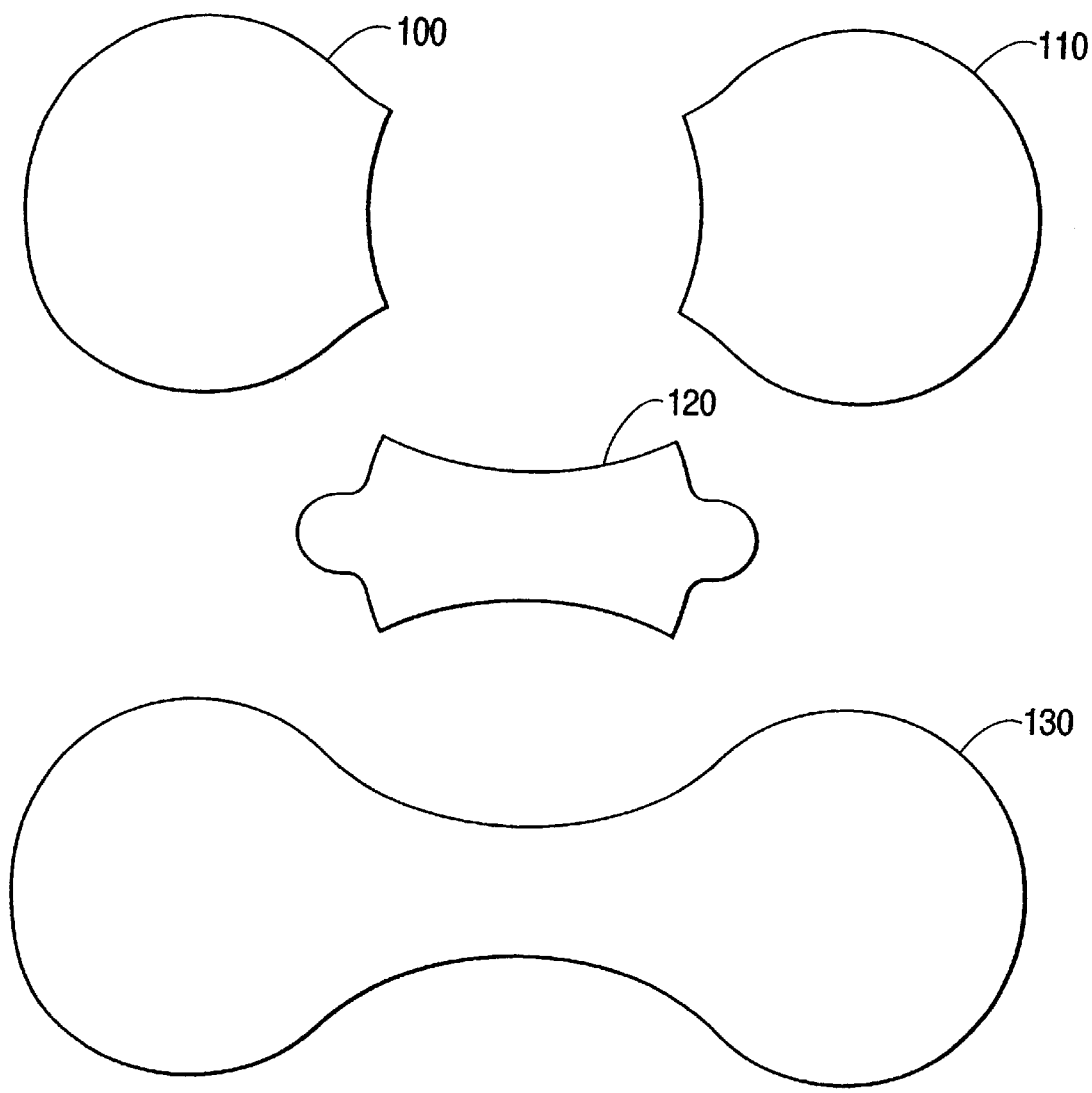
FIG. 1 illustrates a set of membranes for use in constructing an ear warmer, according to an embodiment of the present invention.

FIG. 1 illustrates a set of membranes for use in constructing an ear warmer, according to an embodiment of the present invention. As shown in FIG. 1, an ear warmer can be constructed from first ear membrane 100, second ear membrane 110, middle membrane 120 and outer membrane 130. Membranes 100 through 130 can be made of various types of material appropriate for providing warmth while also being comfortable on the wearer's skin. For example, membranes 100 through 130 can be made of such materials as fleece, wool, cotton, foam and/or neoprene.

FIG. 2 illustrates an arrangement of an ear warmer shell during an interim step in an assembly process, according to an embodiment of the present invention. Ear warmer shell 200 includes an arrangement of membranes 100 through 130 where they have been attached together via attachment 140 along the perimeter of the collection of membranes (i.e., along the perimeter of ear warmer 200). Attachment portion 205 is the portion of membranes 100 through 130 between and including attachment 140 and the edge of membranes 100 through 130. For example, when ear warmer membranes 100 through 130 are attached by sewing the membranes together along their collective perimeter, attachment portion 205 is the extra portion of the membranes between the sewn seam and the outer edge of the membranes.

More specifically, ear warmer shell 200 can be constructed by first disposing first ear membrane 100 and second ear membrane 110 on top of outer membrane 130. Middle membrane 120 can then be placed on top of the set of outer membrane 130, ear membrane 100 and ear membrane 110 in the arrangement shown in FIG. 2. Ear membranes 100 and 110, and middle membrane 120 are on top of each other and outer membrane 130 in the sense that they are ordered in a particular way; the particular orientations of the collection of membranes as shown in the figures herein are not important. The arrangement of membranes 100 through 130 can then be attached along the perimeter of ear warmer 200 via attachment 140. A portion of the perimeter of ear membrane 100 is not attached to outer membrane 130; this unattached perimeter portion is labeled as 101. Similarly, a portion of the perimeter of ear membrane 110 is not attached to outer membrane 130; this unattached perimeter portion is labeled as 111.

FIGS. 2, 3, 4 and 5 illustrate ear warmer shell 200 at different steps in a method for assembling an ear warmer, according to an embodiment of the present invention. As shown in FIG. 3, ear warmer shell 200 includes a first ear portion 210, a second ear portion 220 and a middle portion 230. First ear portion 210 includes opening 240 that is formed by the perimeter portion 101 of ear membrane 100. Similarly, second ear portion 220 includes opening 250 that is formed by the perimeter portion 111 of ear membrane 110.

Channel 260 is formed by middle portion 120 and the portion of outer membrane 130 disposed with middle membrane 120. More specifically, middle membrane 120 is attached along two portions 121 and 122 of its perimeter to outer membrane 130 while the two remaining portions 123 and 124 of the perimeter of middle membrane 120 are not attached to outer membrane 130. These unattached perimeter portions of middle membrane 120 generally correspond to openings 240 and 250, thus channel 260 is formed between the attached perimeter portions of middle membrane 120 from opening 240 to opening 250.

As shown in FIG. 3, ear portion 210 can be turned inside out through opening 240. More specifically, line 270 shows the direction in which ear portion 210 should be moved to turn it inside out. The outer edge 210A of ear portion 210 is moved through opening 240 so that ear portion 210 is turned inside out. In otherwords, an interior formed by ear membrane 100 and outer membrane 130 is turned outward by moving the end 210A of ear portion 210 along line 270 through opening 240 and then completely turned outward as shown in FIG. 4. In this manner, attachment 140 (e.g., an externally sewn seam) along the perimeter of ear portion 210 is turned inward so that a portion of the attachment 140 is located within a newly defined interior portion of ear portion 210. Consequently, this portion of attachment 130 is not visible from the outside of ear warmer shell 200, and rather is internal to ear warmer shell 200.

FIG. 4 illustrates another step for assembling an ear warmer according to an embodiment of the present invention. The outer edge 220A of ear portion 220 is turned inside out along line 280 so that the outer edge of ear portion 220 is moved through channel 260 and through opening 240. Once ear portion 220 is partially turned inside out within channel 260, it can be further moved along motion line 280 through the use of an additional device such as a dowel so that ear portion 220 can completely transit the channel 260 and be moved through opening 240.

Note that as ear portion 220 is turned inside out as described above in reference to FIG. 4, the middle portion 230 is also turned inside out. In other words, as the outer edge of ear portion 220 is turned inside out, the middle portion 230 is moved through its channel 260 and through opening 240. Consequently, middle portion 230 is turned inside out so that the exterior sides of middle portion 230 as shown in FIGS. 2 and 3 are now interior to ear warmer shell 200 as shown in FIG. 4.

Figure 5:
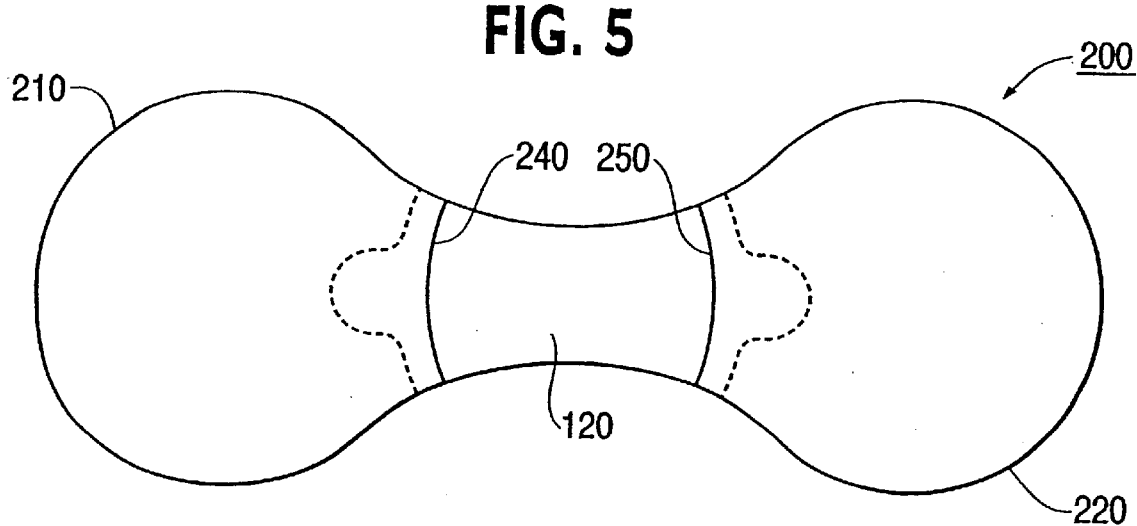

The unattached portions 125 and 126 of middle membrane 120 can then be placed through the respective openings 240 and 250 so that the ends of middle membrane 120 (shown, for example, as having tabs in FIGS. 3–5) are not visible from the outside but rather are disposed within the interior formed by ear membrane 100 and outer membrane 130 on one side of ear warmer shell 200 and formed by ear membrane 110 and outer membrane 130 are on the other end of ear warmer shell 200. Thus, as shown in FIG. 5, attachment 140 (e.g., the sewn seams) that was externally visible as the membranes were initially attached along the outer perimeter of ear warmer shell 200 (as illustrated, for example, in FIG. 2) are now all internal to ear warmer shell 200 and not visible from the exterior as shown in FIG. 5. In such a case, ear warmer shell 200 has a different appearance from that disclosed in U.S. Pat. No. 5,835,609 while yet being an aesthetically pleasing appearance and also obviating the need for binding over an external seam.

FIG. 6 illustrates a top view of a frame that can be disposed within an ear warmer shell to form an ear warmer, according to an embodiment of the present invention. Frame 300 includes a first frame member 310, a second frame member 310 and a third frame member 320. Frame member 320 can be, for example, a slidably adjustable band having an inner curved side 321 and an outer curved side 322. U.S. Pat. No. 5,835,609 discloses an example of frame 300 including frame members 310 and 320 and is incorporated herein by reference (see, e.g., FIGS. 28–38 and the associated written description in U.S. Pat. No. 5,835,609). Connection device 330 (such as a rivet) can attach frame members 310 to frame member 230.

Figure 7:
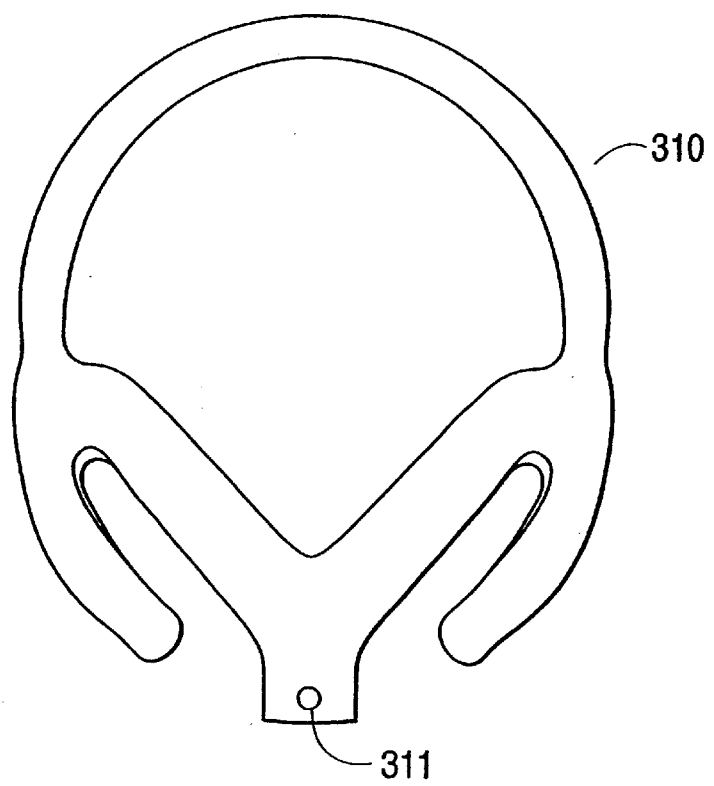
FIG. 7 illustrates a frame member of a frame to be inserted into an ear warmer shell, according to an embodiment of the present invention.

FIG. 7 illustrates a frame member of a frame to be inserted into an ear warmer shell, according to an embodiment of the present invention. More specifically, frame member 310 can have a frusto-conical shape that is conducive to being comfortably placed against a user's ear. Frame member 310 can include a connection portion 311. In the embodiment shown in FIG. 7, the connection portion 311 can include a rivet hole that aligns with a similar rivet hole in third frame member 320 (shown in FIG. 6); connection device 330 can then attach frame members 310 to frame member 320 via their respective connection portions 311. Alternatively, a connection portion of a frame member (similar in function to connection portion 311 and connection device 330 of frame member 300) can be an integral snap-fit connector that complementarily fits with an associated portion on a band-like frame member (similar to frame member 320).

The unattached frame members of frame 300 can be inserted into ear warmer shell 200 and then attached together by the following steps. First, a frame member 310 can be inserted into ear portion 210 through opening 240. Similarly, a second frame member 310 can be inserted in ear portion 220 through opening 250. Of course, frame members 310 can be oriented with respect to the membranes (and the wearer's head) appropriately; for example, outer membrane 130 can be positioned along the rear, outward facing (i.e., not adjacent to the wearer's head) with respect to the ear warmer. In such a case, the frame members 310 should be inserted into the respective interiors of ear portions 210 and 220 such that the relative base of the frusto-conical shape of frame members 310 is disposed towards the wearer's ears (i.e., the curvature of frame member 310 is similar to the wearer's head). Similarly, middle membrane 120 should be disposed inwardly adjacent to the wearer's head when the ear warmer is completely assembled and worn by the wearer.

In the next step in the method for inserting the frame, frame member 320 can be inserted into channel 260 through either opening 240 or 250. Again, frame member 320 should be disposed within channel 260 so that the curvature of frame member 320 is similar to the curvature of the user's head.

The ends of frame members 310 can be connected to the respective ends of frame member 320. Once frame members 310 and frame member 320 are appropriately positioned within the interior of ear warmer shell 200, connection portion 311 of frame member 310 can be disposed through opening 240 along with the corresponding end of frame member 320 so that frame member 310 and frame member 320 can be attached by connection devices 330. The other end of frame member 320 can likewise be attached to the other frame member 310.

Once the three frame members are attached to form frame 300, the ear warmer shell 200 can be arranged so that frame 300 is completely disposed within the interior ear warmer shell 200 and is not visible from the exterior. This can be accomplished, for example, by disposing the respective connected ends of frame members 310 and frame member 320 back into the interior ear warmer shell 200. The tab-like ends of middle membrane 120 can then be reinserted into openings 240 and 250 so that the assembling of the ear warmer including its ear warmer shell 200 and frame 300 is complete.

Figure 8:
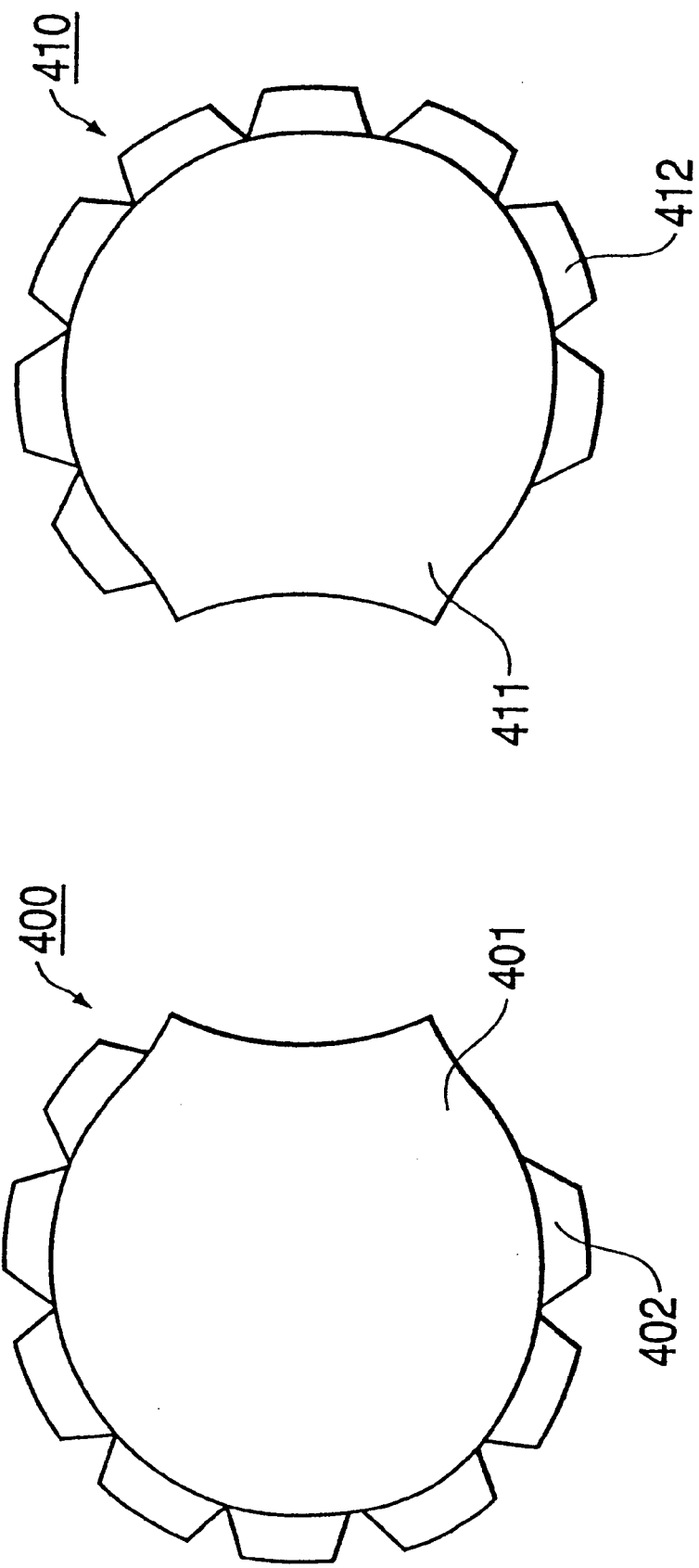
FIG. 8 illustrates ear membranes according to an alternative embodiment of the present invention.

FIG. 8 illustrates ear membranes according to an alternative embodiment of the present invention. Ear membrane 400, as shown in FIG. 8, includes central portion 401 and extended portions 402. Likewise, ear membrane 410 includes central portion 411 and extended portions 412. Note, although only one extended portion is labeled as 402 for ear membrane 400 and, similarly, only one extended portion is labeled 412 for ear membrane 410 in FIG. 8, this notation in FIG. 8 is merely for convenience and would apply to one or more extended portions as appropriate.

Ear membranes 400 and 410 can be substituted for ear membranes 100 and 110 as described in the apparatus and method described above in reference to FIGS. 1–7. In such an embodiment, the perimeter seams discussed in conjunction with FIG. 2 above would be formed along the partial perimeter of central portion 401 and 411 of ear membranes 400 and 410, respectively. In other words, extended portions 402 and 412 of ear membranes 400 and 410, respectively, are disposed outside of the collective perimeter for the ear warmer shell.

When the ear warmer shell is then turned inside out, for example as discussed above in reference to FIGS. 3–5, the extended portions 402 and 412 of ear membranes 400 and 410, respectively, are located within the interior of the ear warmer shell and form an additional layer of fabric. For example, FIG. 9 illustrates the extended portions of the ear membranes forming an added layer of fabric within the interior of the ear warmer shell.

Figure 9:
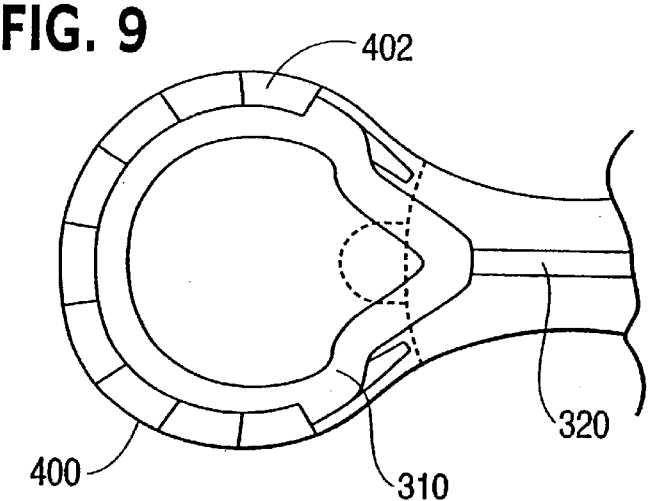
FIG. 9 illustrates a top view of a left portion of an ear warmer, according to an embodiment of the present invention.

More specifically, FIG. 9 illustrates a left portion of an ear warmer, according to an embodiment of the present invention. As illustrated in FIG. 9, the ear portion of the left side of FIG. 9 has the extended portions 402 (shown in phantom) of ear membrane 400 being disposed within the interior of an ear warmer shell such that they form a nearly continuous piece of additional fabric. In such a case, the frame member 310 (shown in phantom) when inserted into an interior of an ear warmer shell can be disposed between extended portions 402 and outer membrane 130. In such an embodiment, extended portions 402 provide an extra layer of cushioning fabric that is disposed between frame member 310 and the wearer's head. In other words, in such an embodiment, extended portions 402 and 412 in addition to central portions 401 and 411 of ear membranes 400 and 410, respectively, are disposed between the wearer and the frame member 310.

Figure 10:
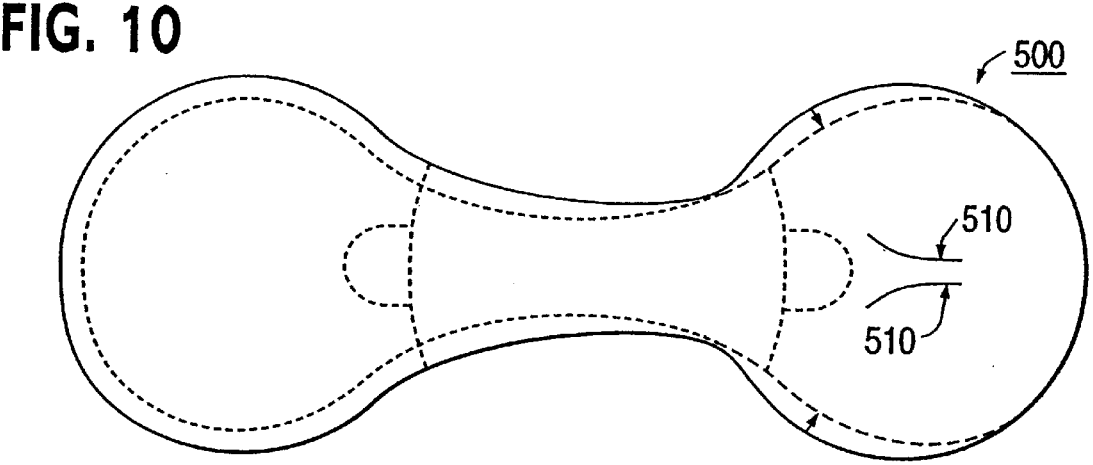
FIG. 10 illustrates a top view of an ear warmer shell, according to another embodiment of the present invention.

FIG. 10 illustrates an ear warmer shell according to another embodiment of the present invention. In such an embodiment of ear warmer shell 500, the ear membranes can have a size slightly smaller than the corresponding portions of the outer membrane. The extra material of the outer membrane portions corresponding to the ear membranes allows the frame (once inserted into the ear warmer shell) to better fit within the ear warmer shell 500. In other words, because the frame to be inserted into the ear warmer shell is curved, the outer curved side (e.g., outer curved side 322 as shown in FIG. 6) of the frame is a greater distance than the inner curved side (e.g., inner curved side 321 as shown in FIG. 6) of the frame. Thus, the extra material of the outer membrane allows the ear warmer shell 500 to better fit around the curved shape of the frame.

The method to construct ear warmer shell 500 is similar to that described above in reference to FIGS. 2–5. Before attaching (e.g., by sewing) the collective perimeter of the membranes, the portion of the outer membrane corresponding to an ear membrane can be pinched inwardly along lines 510 to gather the perimeter of the outer membrane to more closely match the corresponding perimeter of the ear membrane. For example, the portion of the outer membrane corresponding to an ear membrane can be pinched and held inwardly with a clip (such as a binder clip), then the collective perimeter of the membranes can be attached. Thus, collective perimeter of the membranes are aligned when the membranes are being attached while allowing the outer membrane to have extra material so that the frame can better fit within the ear warmer shell 500.

Figure 11:
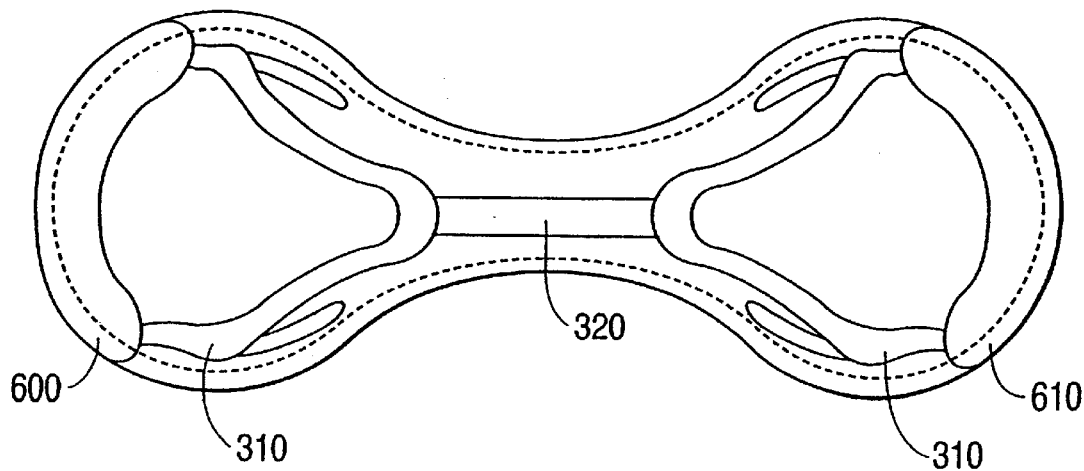
FIG. 11 illustrates internal components of an ear warmer shell, according to yet another embodiment of the present invention.

FIG. 11 illustrates internal components of an ear warmer shell, according to yet another embodiment of the present invention. For purposes of clarity, a covering portion of the ear warmer has been removed to show the internal components of the ear warmer. In this embodiment of an ear warmer shell, pocket membranes 600 and 610 (shown in phantom) are included. In such an embodiment, these additional and separate membranes, i.e., pocket membranes 600 and 610, can be attached (shown in phantom) along the respective portions of the collective perimeter of the ear warmer shell. In other words, pocket membranes 600 and 610 are attached to respective portions of outer membrane 130 and each form a respective pocket into which a frame member 310 can be inserted. The pocket membranes 600 and 610, provide additional cushioning between frame members 310 (shown in phantom) and the head of the user. In such an embodiment, pocket membranes 600 and 610 would be attached on top of the respective ear membranes. Thus, when the ear warmer shell is turned inside out (as described above, for example, in reference to FIGS. 3–5), pocket membranes 600 and 610 are appropriately positioned within the ear warmer shell.

FIG. 12 illustrates a set of membranes for use in constructing an ear warmer, according to another embodiment of the present invention. Similar to the outer membrane 130 and the middle membrane 120 shown in FIG. 1, FIG. 12 illustrates a membrane having an outer portion 730 and a middle portion 720. The membranes can be arranged as follows. First, the ear membranes (e.g., ear membranes 100 and 110) can be placed on the corresponding portions of outer portion 730, i.e., portions 731 and 732 of outer portion 730. Middle portion 720 can then be folded on to outer portion 730 along the line 725. The collective perimeter can then be attached and the membranes can be turned inside out as described above in reference to FIGS. 3–5.

FIG. 13 illustrates a membrane for use in constructing an ear warmer, according to yet another embodiment of the present invention. Similar to ear membrane 100, ear membrane 110, middle membrane 120 and outer membrane 130 shown in FIG. 1, FIG. 13 illustrates a membrane having ear portion 800, ear portion 810, middle portion 820 and outer portion 830. The membrane portions can be arranged as follows. First, the ear portions 800 and 810 can be folded onto the corresponding portions of outer portion 830 along lines 805 and 815, respectively. Middle portion 820 can then folded on to outer portion 830 along the line 825. The collective perimeter can then be attached and the membranes can be turned inside out as described above in reference to FIGS. 3–5.

Rather than the separate membranes shown in FIG. 1, variations to FIGS. 12 and 13 are possible where certain membranes are integrally formed together and folded over. For example, in another embodiment, only one ear membrane is integrally formed with the outer membrane, only two ear membranes are integrally formed with the outer membrane, or only one ear membrane and the middle membrane are integrally formed with the outer membrane.

In another alternative embodiment, the membranes can be integrally formed together at various locations (e.g., discontinuous locations) rather than along the entire fold (such as line 725 shown in FIG. 12). In yet another embodiment, the membranes can be integrally formed at various locations relative to the outer portion of the membrane. For example, rather than the ear portions being integrally formed at the lower location of the outer portion (as shown in FIG. 13), the ear portions can be integrally formed with the outer portion at other locations, such as the side locations 830A and 830B of the outer portion. The various locations that are possible are those where the portions of the membrane (i.e., the middle portion, and/or the ear portions) fold on to the outer portion of the membrane to appropriately form the ear warmer shell.

It should, of course, be understood that while the present invention has been described in reference to particular configurations, other configurations will be apparent to those of ordinary skill in the art. For example, the membranes and frame members can be made of any type of materials appropriate for an ear warmer device. U.S. Pat. No. 5,835, 609, which is incorporated herein by reference, discloses various embodiments of the ear warmer device and those variations can be combined with the method and apparatus described herein.

What is claimed is:

1. An ear warmer, comprising:
   a plurality of membrane portions collectively defining an outer perimeter, said plurality of membrane portions being attached along said outer perimeter to define an attachment having a side along said outer perimeter, said side of said attachment along said outer perimeter being entirely disposed within an interior of said plurality of membrane portions; and
   a frame disposed within said interior of said plurality of membrane portions.

2. The ear warmer of claim 1, wherein said plurality of membrane portions includes:
   an outer membrane portion; and
   an ear membrane portion being integrally formed with said outer membrane portion along a first portion of said ear membrane portion, a second portion of said ear membrane portion being attached to said outer membrane portion along a first portion of said outer perimeter and within a first portion of said interior.

3. The ear warmer of claim 1, wherein said plurality of membrane portions includes:
   an outer membrane portion;
   an ear membrane portion being integrally formed with said outer membrane portion along a first portion of said ear membrane portion, a second portion of said ear membrane portion being attached to said outer membrane portion along a first portion of said outer perimeter and within a first portion of said interior; and
   a middle membrane portion being integrally formed with said outer membrane portion along a first portion of said middle membrane portion, a second portion of said middle membrane portion being attached to said outer membrane portion along a second portion of said outer perimeter and within a second portion of said interior.

4. The ear warmer of claim 1, wherein said plurality of membrane portions are attached along an entirety of said outer perimeter.

5. The ear warmer of claim 1, wherein said frame is disposed entirely within said interior of said plurality of membrane portions.

6. The ear warmer of claim 1, wherein said plurality of membrane portions includes an outer membrane portion and an ear membrane portion, said outer membrane portion including a portion corresponding to said ear membrane portion, said corresponding portion being larger than said ear membrane portion.

7. The ear warmer of claim 1, wherein said plurality of membrane portions includes an outer membrane portion and an ear membrane portion, said outer membrane portion including a portion corresponding to said ear membrane portion, said corresponding portion being larger than said ear membrane portion, said corresponding portion and said ear membrane portion having corresponding perimeters.

8. An ear warmer, comprising:
   an ear warmer shell including a plurality of membranes each having an edge portion that is disposed adjacent to an edge portion of a remaining membrane from said plurality of membranes, said plurality of membranes each being attached along the adjacently-disposed edge portions to define an attachment having an outer side, said outer side of said attachment being entirely disposed within an interior of said plurality of membranes; and
   a frame disposed within said interior of said plurality of membranes.

9. The ear warmer of claim 8, wherein said plurality of membranes includes:
   an outer membrane;
   a first ear membrane attached to said outer membrane along a first portion of said outer membrane and defining a first interior portion of said ear warmer shell, said first ear membrane being attached within said first interior portion;
   a second ear membrane attached to said outer membrane along a second portion of said outer membrane and defining a second interior portion of said ear warmer shell, said second ear membrane being attached within said second interior portion; and
   a middle membrane attached to said outer membrane along a third portion of said outer membrane and defining a third interior portion of said ear warmer shell, said middle membrane being attached within said third interior portion.

10. The ear warmer of claim 8, wherein said plurality of membranes are attached along an entirety of said edge portions.

11. The ear warmer of claim 8, wherein said frame is disposed entirely within said interior of said plurality of membranes.

12. The ear warmer of claim 9, wherein said outer membrane, said first ear membrane, said second ear membrane, and said middle membrane are integrally formed.

13. The ear warmer of claim 8, wherein said plurality of membranes includes an outer membrane and an ear membrane, said outer membrane including a portion corresponding to said ear membrane, said corresponding portion being larger than said ear membrane.

14. The ear warmer of claim 8, wherein said plurality of membranes includes an outer membrane and an ear membrane, said outer membrane including a portion corresponding to said ear membrane, said corresponding portion being larger than said ear membrane, said corresponding portion and said ear membrane having corresponding perimeters.

15. An ear warmer, comprising:
a one-piece membrane having a first ear portion, a second ear portion, a middle portion, and an outer portion, said first ear portion, said second ear portion, said middle portion, and said outer portion being adapted to collectively define therebetween an interior of said membrane, said outer portion having a first portion corresponding to said first ear portion and a second portion corresponding to said second ear portion; and
a frame disposed within said interior of said membrane.

16. The ear warmer of claim 15, wherein said first ear portion, said second ear portion, and said middle portion are integrally formed with said outer portion.

17. The ear warmer of claim 15, wherein said first ear portion is integrally formed with a side of said outer portion proximate to an end of said outer portion.

18. The ear warmer of claim 15, wherein said first ear portion is integrally formed with a first side of said outer portion proximate to a first end of said outer portion, and said second ear portion is integrally formed with a second side of said outer portion proximate to a second end of said outer portion.

19. The ear warmer of claim 15, wherein said first ear portion, said second ear portion, and said middle portion are integrally formed with said outer portion at a plurality of discontinuous locations.

20. The ear warmer of claim 15, wherein said first ear portion, said second ear portion, and said middle portion are attached along an entirety of a perimeter of said outer portion.

21. The ear warmer of claim 15, wherein said first ear portion and said middle portion are integrally formed with opposite sides of said outer portion.

22. The ear warmer of claim 15, wherein said first ear portion has the same configuration as said first corresponding portion of said outer portion.

23. The ear warmer of claim 15, wherein said first ear portion has the same configuration as said first corresponding portion of said outer portion, and said second ear portion has the same configuration as said second corresponding portion of said outer portion.

24. The ear warmer of claim 15, wherein said first ear portion, said second ear portion, said middle portion, and said outer portion collectively define an outer perimeter and are attached along said outer perimeter to define an attachment having a side along said outer perimeter, said side of said attachment along said outer perimeter being entirely disposed within said interior of said membrane.

25. The ear warmer of claim 15, wherein said first ear portion is coupled to said outer portion, said second ear portion is coupled to said outer portion, said first ear portion being separate from said second ear portion.

26. The ear warmer of claim 15, wherein said first ear portion, said second ear portion, and said middle portion are separate from each other.

27. A method of forming an ear warmer using a membrane having a first ear portion, a second ear portion, a middle portion, and an outer portion, the method comprising the steps of:
disposing the membrane to form an interior between the first ear portion, the second ear portion, the middle portion, and the outer portion; and
disposing a frame within the interior of the membrane.

28. The method of claim 27, wherein said disposing the membrane includes:
folding the first ear portion onto a first corresponding portion of the outer portion;
folding the second ear portion onto a second corresponding portion of the outer portion; and
folding the middle portion onto the outer portion.

29. The method of claim 27, wherein said disposing the membrane includes:
folding the first ear portion onto a first corresponding portion of the outer portion;
folding the second ear portion onto a second corresponding portion of the outer portion;
folding the middle portion onto the outer portion; and
attaching the middle portion to a portion of a remaining perimeter of the outer portion.

30. The method of claim 27, wherein said disposing the membrane includes:
folding the first ear portion onto a first corresponding portion of the outer portion;
folding the second ear portion onto a second corresponding portion of the outer portion;
folding the middle portion onto the outer portion;
attaching the middle portion to a portion of a remaining perimeter of the outer portion;
attaching the first ear portion to a portion of a remaining perimeter of the first corresponding portion; and
attaching the second ear portion to a portion of a remaining perimeter of the second corresponding portion.

31. The method of claim 28, wherein said disposing a frame within the interior includes:
disposing a frame member between the first ear portion and the first corresponding portion of the outer portion; and
disposing a frame member between the second ear portion and the second corresponding portion of the outer portion.

32. The ear warmer of claim 15, wherein said first ear portion has a perimeter and being attached to said outer portion along part of said first ear portion perimeter, and said second ear portion has a perimeter and being attached to said outer portion along part of said second ear portion perimeter.

33. The ear warmer of claim 15, wherein said middle portion has a perimeter, said middle portion being attached to said outer portion along part of said middle portion perimeter, said middle portion being attached to said outer portion between said first ear portion and said second ear portion.

34. The ear warmer of claim 15, wherein said first ear portion is attached to said outer portion proximate to said first corresponding portion.

35. The ear warmer of claim 32, wherein said first ear portion is attached to said outer portion proximate to said first corresponding portion, said second ear portion is attached to said outer portion proximate to said second corresponding portion.

36. The ear warmer of claim 15, wherein said middle portion has a perimeter, said middle portion being attached to said outer portion along part of said middle portion.

37. An ear warmer, comprising:

an ear warmer shell including:

an outer membrane;

an ear membrane, said ear membrane being attached to said outer membrane, said ear membrane and said outer membrane collectively defining an outer perimeter, said ear membrane and said outer membrane defining therebetween an interior of said ear warmer shell; and a pocket membrane, said pocket membrane disposed within said interior of said ear warmer shell, said pocket membrane being attached along a portion of said outer perimeter; and a frame disposed within said interior of said ear warmer shell.

38. The ear warmer of claim 37, wherein said pocket membrane is attached between said ear membrane and said outer membrane along a portion of said outer perimeter.

39. The ear warmer of claim 37, wherein said pocket membrane and said outer membrane define a pocket therebetween.

40. The ear warmer of claim 37, wherein said pocket membrane and said outer membrane define a pocket therebetween, said frame being inserted into said pocket.

41. A method of forming an ear warmer shell using a membrane having an ear membrane portion and an outer membrane portion, the ear membrane portion having an outer perimeter, the outer membrane portion having an outer perimeter, the outer membrane portion including a portion corresponding to the ear membrane portion, the corresponding portion being larger than the ear membrane portion, the method comprising the steps of:

disposing the ear membrane portion proximate to the corresponding portion of the outer membrane portion;

moving a first portion of the outer membrane portion and a second portion of the outer membrane portion together inwardly; and attaching the ear membrane portion and the outer membrane portion.

42. The method of claim 41, wherein said moving a first portion includes:

moving the outer perimeter of the corresponding portion inwardly so that the outer perimeter of the corresponding portion of the outer membrane and the outer perimeter of the ear membrane portion are substantially aligned.

* * * * *

UNITED STATES PATENT AND TRADEMARK OFFICE
CERTIFICATE OF CORRECTION

PATENT NO.    : 6,502,247 B2
DATED         : January 7, 2003
INVENTOR(S)   : Brian Edward Le Gette and Justin Saul Werner It is certified that error appears in the above-identified patent and that said Letters Patent is hereby corrected as shown below:

Title page,
Item [56], References Cited, section include:
-- FOREIGN PATENT DOCUMENTS
GB 1,327,614   8/1973 --

Column 1,
Line 18, change "protection" to -- Protection --;

Column 9,
Line 54, change "car" to -- ear --;

Column 10,
Line 39, change "car" to -- ear --; and

Column 36,
Line 63, change "car" to -- ear --.

Signed and Sealed this

Twelfth Day of August, 2003

JAMES E. ROGAN
*Director of the United States Patent and Trademark Office*